US011784969B2

(12) United States Patent
Tobias

(10) Patent No.: US 11,784,969 B2
(45) Date of Patent: Oct. 10, 2023

(54) SYSTEM FOR SECURELY MONITORING AND EXTRACTING DATA THROUGH A PRIVATE NETWORK

(71) Applicant: Phrase Health, Inc., Philadelphia, PA (US)

(72) Inventor: Marc Tobias, Philadelphia, PA (US)

(73) Assignee: Phrase Health, Inc., Philadelphia, PA (US)

( * ) Notice: Subject to any disclaimer, the term of this patent is extended or adjusted under 35 U.S.C. 154(b) by 454 days.

(21) Appl. No.: 17/207,494

(22) Filed: Mar. 19, 2021

(65) Prior Publication Data

US 2021/0297387 A1    Sep. 23, 2021

Related U.S. Application Data

(60) Provisional application No. 62/992,780, filed on Mar. 20, 2020.

(51) Int. Cl.
| | |
|---|---|
| *H04L 9/40* | (2022.01) |
| *G06F 9/451* | (2018.01) |
| *G06F 16/245* | (2019.01) |
| *G16H 10/60* | (2018.01) |

(52) U.S. Cl.
CPC .............. *H04L 63/02* (2013.01); *G06F 9/451* (2018.02); *G06F 16/245* (2019.01); *G16H 10/60* (2018.01); *H04L 63/0272* (2013.01)

(58) Field of Classification Search
CPC ......... H04L 63/02; G06F 9/451; G06F 16/245
See application file for complete search history.

(56) References Cited

U.S. PATENT DOCUMENTS

| | | | | |
|---|---|---|---|---|
| 8,515,989 | B2* | 8/2013 | Fernandez | G16H 10/60 707/940 |
| 8,751,252 | B2* | 6/2014 | Chamberlain | G16H 10/60 705/2 |
| 9,589,105 | B2* | 3/2017 | Allen | G06F 11/0751 |
| 10,050,938 | B2* | 8/2018 | Moskow | H04L 63/0263 |
| 10,257,226 | B2* | 4/2019 | Drummond | H04W 12/122 |
| 10,270,744 | B2* | 4/2019 | Yu | H04L 63/1441 |
| 10,826,925 | B2* | 11/2020 | Mesic | H04L 63/20 |
| 10,908,970 | B1* | 2/2021 | Arivazhagan | G06F 9/54 |
| 10,951,645 | B2* | 3/2021 | Mathew | H04L 41/142 |

(Continued)

*Primary Examiner* — Viral S Lakhia
(74) *Attorney, Agent, or Firm* — Knobbe, Martens, Olson & Bear, LLP

(57) ABSTRACT

Systems and methods are described for secure data extraction through a private network. A data extraction application may operate behind a firewall on a client system. Application state information may be automatically gathered and sent by the data extraction application upon the data extraction application being awakened at a predetermined time. A remote system outside of a firewall may determine commands to return to the data extraction application that include one or more query parameters, and then send the commands to the data extraction application. The remote system may then obtain, from the client system behind the firewall or from a data store outside of the firewall, results of the data extraction application executing a query with the provided query parameters injected therein, where the query was executed by the data extraction application with respect to one or more files located behind the firewall.

12 Claims, 13 Drawing Sheets

(56) References Cited

U.S. PATENT DOCUMENTS

| | | | |
|---|---|---|---|
| 11,243,972 B1* | 2/2022 | Frakes | G06F 17/18 |
| 2016/0191549 A1* | 6/2016 | Nguyen | H04L 43/12 |
| | | | 726/23 |
| 2020/0192862 A1* | 6/2020 | Tsai | G06F 16/162 |
| 2021/0034767 A1* | 2/2021 | Free | G06F 21/86 |

* cited by examiner

Phrase Health  ADMINISTRATOR Add Organization

◉ Health System 1 ✏ ⓘ
Run March 16, 2020
Files 220 of 220
Next Run 20:00 EST

◉ Health System 2 ✏ ⓘ
Run March 16, 2020
Files 218 of 218
Next Run 16:00 EST

◉ Health System 3 ✏ ⓘ
Run March 16, 2020
Files 220 of 220
Next Run 21:00 EST

◉ Health System 4 ✏ ⓘ
Run March 17, 2020
Files 228 of 228
Next Run 8:00 EST

◉ Health System 5 (in progress) ✏ ⓘ
▒▒▒▒▒▒▒

◉ Health System 6 ✏ ⓘ
Run March 16, 2020
Files 220 of 220
Next Run 17:00 EST

◎ Health System 7 (errors) ✏ ⓘ
Run
Files 0 of 0
Next Run Not setup

| Phrase Health | ADMINISTRATOR | | | |
|---|---|---|---|---|
| Dashboard / Health System 1 | | | | |
| Extraction | Processes | SQL Files | | |
| ETL | | | | |

| | Process ID ⇅ | Start ⇅ | End ⇅ | Success % ⇅ |
|---|---|---|---|---|
| DAILY | 7818dedaa319146daa0cb65269982a1b | 03/16/2020 | 03/17/2020 | 100 |
| DAILY | da35713f541937f00f0f7aa4269d973b | 03/15/2020 | 03/16/2020 | 100 |
| DAILY | abe97a42a87c708c475fbbbda5252702 | 03/14/2020 | 03/15/2020 | 100 |
| DAILY | e0710faec2b068e315551a3620b422e9 | 03/13/2020 | 03/14/2020 | 100 |
| DAILY | f2bb1975eea3fe89523e5107f642be24 | 03/12/2020 | 03/13/2020 | 100 |
| DAILY | 520d8c1acb0876891890e3ababc7df31 | 03/11/2020 | 03/12/2020 | 0 |
| DAILY | 54b9eaaa195788fb4175fa47d42a096e | 03/10/2020 | 03/11/2020 | 100 |
| DAILY | 8a91c6df836d574f62c80582429a3f11 | 03/09/2020 | 03/10/2020 | 100 |
| DAILY | 6aed322d4b415bb0cfa5ca47ba59cf32 | 03/08/2020 | 03/09/2020 | 100 |
| DAILY | 83a843c8c70311ac5f1ef1ca979edff5 | 03/07/2020 | 03/08/2020 | 100 |

Phrase Health   ADMINISTRATOR

Dashboard / Health System 1 / 7818dedaa319146daa0cb65269982a1b

Extraction ETL | Processes | SQL Files

Run Files  March 17, 2020  228 of 228

Search SQL Files

| File | Start | End |
|---|---|---|
| FILE1.sql | 2020-03-16 | 2020-03-17 |
| FILE2.sql | 2020-03-16 | 2020-03-17 |
| FILE3.sql | 2020-03-16 | 2020-03-17 |
| FILE4.sql | 2020-03-16 | 2020-03-17 |
| FILE5.sql | 2020-03-16 | 2020-03-17 |
| FILE6.sql | 2020-03-16 | 2020-03-17 |
| FILE7.sql | 2020-03-16 | 2020-03-17 |
| FILE8.sql | 2020-03-16 | 2020-03-17 |
| FILE9.sql | 2020-03-16 | 2020-03-17 |
| FILE10.sql | 2020-03-16 | 2020-03-17 |
| FILE11.sql | 2020-03-16 | 2020-03-17 |
| FILE12.sql | 2020-03-16 | 2020-03-17 |
| FILE13.sql | 2020-03-16 | 2020-03-17 |

« < 1 2 3 4 ... > »

---

FILE1.sql   ✕

Dates 2020-03-16 to 2020-03-17
Records 36805
Time 161.84 seconds

Extract File Path   ⧉ view
s3://phxxxxxx20200317-FILE1.csv.gz

Log File Path   ⧉ view
s3://phrasxxxxxxx/daily20200317/
7818dedaa319146daa0cb65269982a1b/FILE1T.log

SQL File Path
s3://phxxxxxxSQL-
FILES/daily20200317/7818dedaa319146daa0cb65269982a1b/
FILE1.sql

FIG. 4C

Phrase Health  ADMINISTRATOR

Dashboard / Health System 1

Extraction | Processes | SQL Files
ETL

Extract Type
On Demand  ◁▷   ← 406

Start Date         End Date
03/16/2020            03/17/2020

2                                    Submit  Clear Selections
files of 228                        ↑ 408

All Date | Non-date | Search files                Select all | UnSelect all

☐ FILE1.sql          ☐ FILE2.sql          ☐ FILE3.sql
☐ FILE4.sql          ☐ FILE5.sql          ☐ FILE6.sql
☐ FILE7.sql          ☐ FILE8.sql          ☐ FILE9.sql

FIG. 4D

Analyst Queue

| Home ▽ | Alerts ▽ | Governance | Projects | Analyst Queue | | All ▽ | Search | Search | Jane Jones ▽ |

MEASURE (NEW)
30 day readmissions
Here is a brief description for this measure
10/10/2020 | Submitted by Joe Smith for Peds Migrane QI     [View Data Request]

COHORT (OPENED)
ED Sepsis Patients
Here is a brief description for this measure
10/10/2020 | Submitted by Jane Jones for Opioid Improvement QI     [View Data Request]

MEASURE (PENDING APPROVAL)
Length of Stay
Here is a brief description for this measure
10/10/2020 | Submitted by John for Peds Migrane QI     [View Data Request]

MEASURE (ERROR)
Length of Stay
Here is a brief description for this measure
10/10/2020 | Submitted by Rob Ray for Peds Migrane QI     [View Data Request]

MEASURE (AVAILABLE)
Length of Stay
Here is a brief description for this measure

FIG. 7A

Home ▾ Alerts ▾ Governance Projects Analyst Queue | All ▾ | Search | Jane Jones ▾

Measure: Length of Stay
○ Status: Request opened

Request details
Requested on          10/10/2020
Requestee             Jane Jones
Contact    jane@example.com
Project    Peds Migraine QI

About the measure
Here is a brief description about this measure blah blah

Submitting a request
1. Meet with the requestee to see if you have any clarifying questions about their request
2. Pull a sample set of data to verify the query meets the needs of the requestee
3. Submit your query for admin approval.

☐ Learn more about requests

Custom Measure Submission Form

Measure Name ⓘ
[Measure name]

Description (seen by end user) ⓘ
[Please thoroughly describe what this measure is in a way that an end user can understand]

Definition ⓘ
[Please thoroughly describe what this measure is in a way that an end user can understand]

Datatype ⓘ
[Boolean]

Database ⓘ
[Organization database]

SQL
[SQL query goes here]

[Submit request]  [Save changes]

SYSTEM FOR SECURELY MONITORING AND EXTRACTING DATA THROUGH A PRIVATE NETWORK

PRIORITY AND INCORPORATION BY REFERENCE

Any and all applications for which a foreign or domestic priority claim is identified in the Application Data Sheet as filed with the present application are hereby incorporated by reference under 37 CFR 1.57.

This application claims benefit of U.S. Provisional Patent Application No. 62/992,780, entitled "SYSTEM FOR SECURELY MONITORING AND EXTRACTING DATA THROUGH A PRIVATE NETWORK," filed Mar. 20, 2020, which is hereby incorporated by reference in its entirety.

BACKGROUND

The extraction and transfer of sensitive health care data is a challenging endeavor. Strong security precautions are taken on behalf of data stewards like hospitals in order to protect their systems from malicious external actors. These precautions invariably entail firewalls placed around internal networks to exclude external access. However, data administrators also need to deploy methods to securely transfer data to approved third-party partners, vendors, or other external stakeholders. All parties are incentivized to lower the burden of installation and maintenance of any adopted method due to limited available resources. For example, a third-party vendor may require a select patient dataset to power an application that a hospital system relies on to deliver quality clinical care. According to existing systems, the vendor will need to define the prerequisite data and then work with the data steward to configure a local process. This typically relies on the data steward defining the extractions and then dumping the resultant data to an external secure repository like a Secure File Transfer Protocol (SFTP) endpoint, which the vendor will then transfer over on their own. Another option is to grant access to the data steward's private network to the third-party vendor and allow them to set up the process themselves.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIGS. 4A-4D illustrate sample administrator dashboard interface features for analyzing performance of a slave application, according to some embodiments.

FIGS. 7A and 7B illustrate sample interface features for customizing, monitoring, and authorizing cloud-based queryable assets, according to some embodiments.

DETAILED DESCRIPTION

The disclosure relates to the secure orchestration of a data extraction system through a private network. For example, aspects of the present disclosure may include gathering and extracting electronic health data from a health provider for cloud-based analytics and analysis to be performed on behalf of the health provider. A data extraction application (which may be considered a slave application) and associated server-side components (which may be considered to provide functionality of a master system to the slave application) enable remotely triggered extraction and upload of electronic health data from behind the firewall of the administrator of an electronic health record system or medical practice's computer system in an automated manner while complying with security constraints of the provider's system. As will be described herein, an extraction application may be installed by a health provider or other data steward (which may refer to a system associated with an individual or organization that is an owner and/or manager of data to be extracted) behind their firewall, the application periodically initiates communication with a server to determine whether the server would like any data extraction to be performed, and if so the server may respond with extraction criteria or parameters that the application behind the firewall uses to gather matching health record data and upload to the server or an external data repository accessible to the operator of the server. It will be appreciated that aspects of the present disclosure are not specific to the medical field, but may be used in a variety of industries in which secure data extraction from a client system is desired.

Figure 1A:
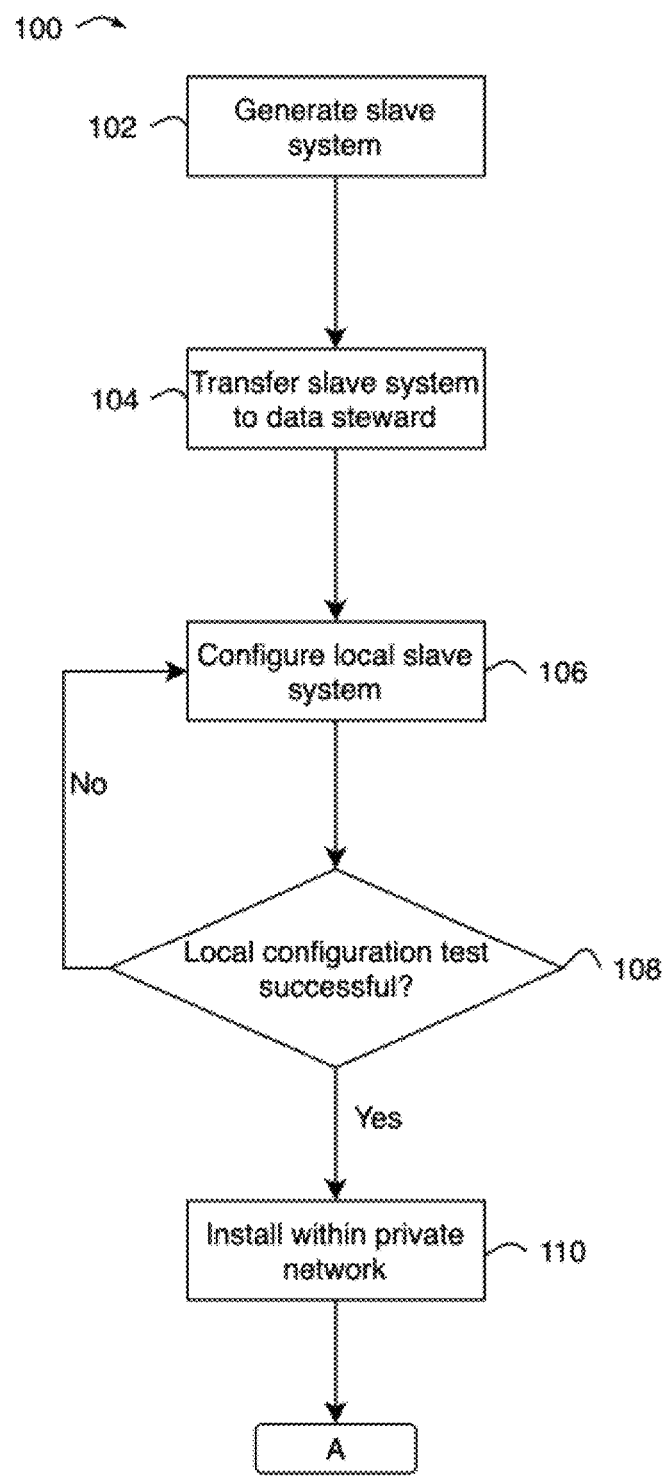
FIGS. 1A and 1B are flow diagrams of an illustrative method for compiling a remote slave system that can follow external instructions to extract data within a secured inaccessible network. This slave system can communicate outside of the network.

FIG. 1A illustrates an example method for configuring and installing components of the system described herein within a private network associated with a data steward. The illustrative method 100 begins at block 102. According to one embodiment, the application is compiled with definitions for where subsequent extracted data should go, drivers to applicable databases, encryption keys, and a unique identifier. The application may be compiled, for example, by an operator of a master system as will be described below, the customer organization, and/or by the data steward. To enable a secure data transfer, relevant security keys and preprogrammed endpoints are defined within the compiled application. This enables secure authentication with an immutable target.

At block 104, the compiled application and associated files are provided to the data steward, such as via electronic delivery over a network. According to one embodiment, this system can be transferred via email or hosted on an external server that the data steward can access.

At block 106, the compiled application may receive additional configuration or setup information, such as at the request of or under control of the data steward. According to one embodiment, a local file defines characteristics including the time of day it should run, how frequently it should be run, periods of the day to avoid, optional days to skip for maintenance, path to queryable assets (e.g. SQL files or other code that can execute a command), the network addresses of available data stores, the credentials of the defined data stores, and the target schemas of the defined data stores. In this example, the time of day to run refers to automated process that will run through all relevant queryable files daily. As data is entered into the configuration, it is encrypted locally. The generation of this configuration file may be completed via a graphical user interface.

At decision block 108, the compiled application uses the configuration to test all facets of its capabilities against the local environment. According to one embodiment, it uses the data store endpoints and credentials to attempt viable connections. In addition, messages are sent to the stored external endpoint using security keys to ensure a secure connection. Any failures in tests are shown to the user to facilitate troubleshooting. If at least one error occurs, the user can again attempt to adjust the configuration.

Next, at block 110, the compiled application is placed on a server within the secure network by the data steward. According to one embodiment, the system is run as an always-on service. This allows for the system to automatically start on any host reboot or reset or otherwise recover from other disruptions.

Figure 1B:
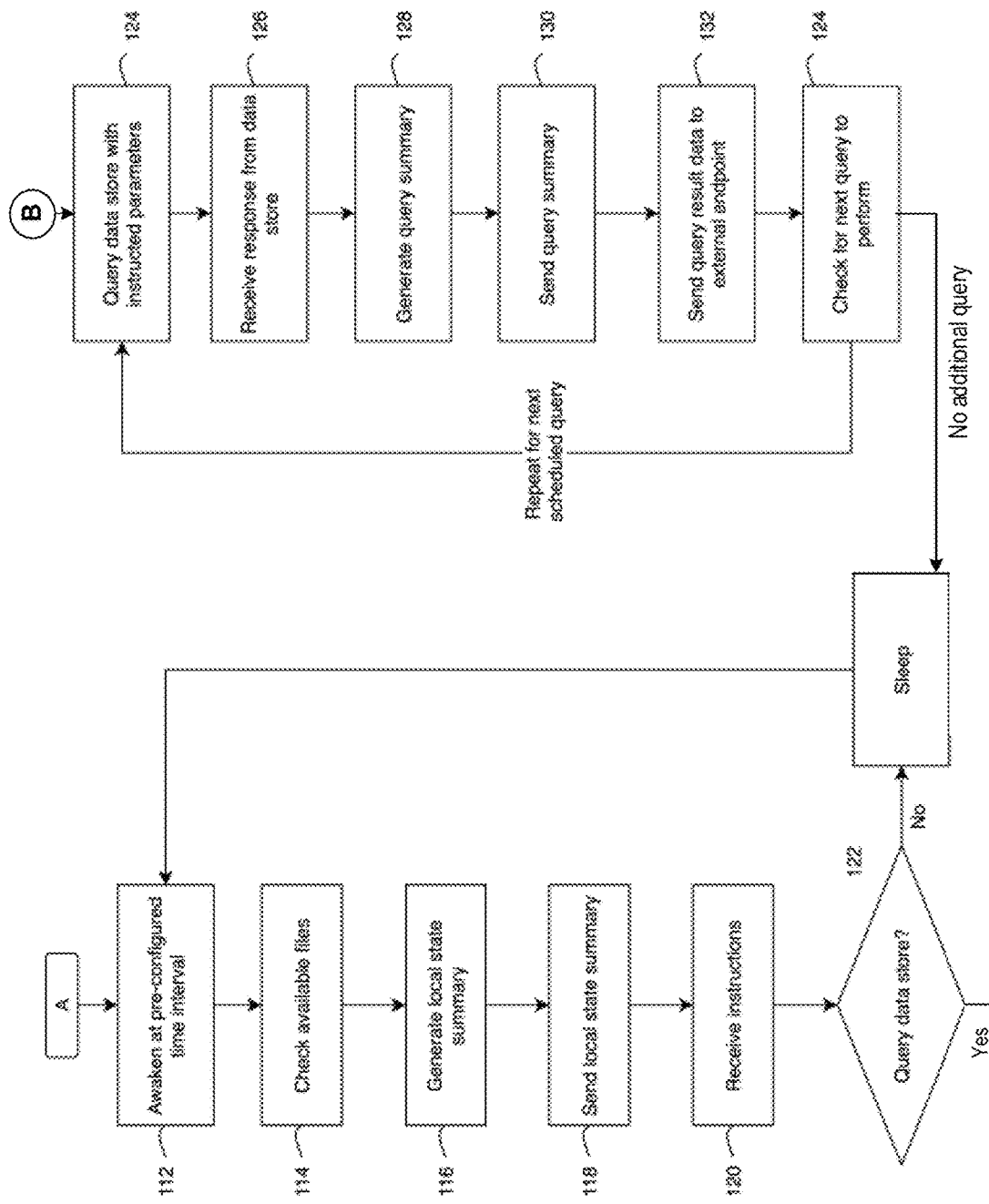

FIG. 1B is a flow diagram continuing the illustrative method 100 discussed above with respect to FIG. 1A. At block 112, the installed slave application is pre-programmed per the local configuration to awake at an interval defined by the local configuration. This configuration setting can be overridden by the master system, in some embodiments. The pre-configured awakening of the slave application enables the start of each potential instance of data extraction to be initiated internally at the source of the data to be extracted (such as behind a firewall), rather than being initiated as an external request from the master system located outside of the firewall (which may not be permitted according to security protocols in place at the data source that may indicate that only outgoing requests are permitted).

In block 114, the slave application evaluates its configured file directory to assess for available queryable files. The external stakeholder creates these files and they are made available to the data steward as previously discussed in block 104. According to one embodiment, the queryable files can be electronically sent (e.g., via email) to the data steward for placement in a local file directory. It is also possible that the queryable files can be hosted remotely (e.g., AWS S3 or other object storage service, blockchain or other distributed ledger, etc.), which would allow for quicker updates to the queryable files in that they wouldn't rely on the data steward to place them locally. In this remote example, there could still be security steps in place to ensure that the data steward approves of the queryable file contents before an extraction is allowed against the data store. An example of a flow diagram that outlines the steps to request, create, approve, and load remote queryable assets is demonstrated and subsequently described below. The slave application can be configured to parse a variety of file formats. According to one embodiment, these queryable files may include a novel format that is derived from structured query language (SQL) with unique parameters like a start date (":startDate:") and an end date (":endDate:"). For example, a file could contain SQL code that requests a set of time series data within a date range, where the date range is parameterized with the ":startDate:"and":endDate:" variables. These parameterized variables are predefined and part of the compiled slave application parser. This file format can also account for characteristics like target name, file version, description, and extracted data file types, which can be subsequently stored in the external system to drive logic for downstream processes. Sample code demonstrating a subset of time series data is outlined here (Code 1):

select id, name from :schema:sampleTable where start_date>=:startDate: and end_date<=:endDate:

These files could also employ other structured formats like JavaScript Object Notation (JSON) to structure the characteristic information about the queryable file. The structure of the derived SQL may also be parameterized to account for different data store requirements (e.g., changing structure of the SQL according to whether configuration is for an Oracle or MS SQL database). The slave application can be compiled to automate the unbundling of grouping file formats. As such, the queryable files may also be bundled into an individual file (e.g., compressed ZIP file) that can contain additional parameters like a bundle version identifier that can be included in the state summary that will be discussed in block 116.

Next, in block 116, the slave system generates a summary of its local state. According to one embodiment, this includes information about the local configuration, information compiled into the system itself, available local queryable files and their associated characteristics, and information about the hosting environment.

In block 118, the configuration summary is sent to the master system for processing. The slave application awaits further instructions. According to one embodiment, this can be transmitted using a representational state transfer (REST) approach that expects a response with relevant information. In one embodiment, this message is sent via a secure 443 port that has been opened for outgoing traffic in the firewall. Additionally, the slave application may send instructions to be stored on the master system regarding expected files to be processed as part of a regularly scheduled process. This sets up a queue of queryable files to be parsed on the master system that the slave can then run through upon future checks.

At decision block 122, the slave application evaluates instructions received from the master system. The generation of these instructions by the master system will be described further below with respect to FIG. 2. If instructions are sent by the master system to utilize the queryable files in the slave application, the slave system will continue to proceed. If no further instructions are received, the slave system will idle until a subsequent pre-configured time interval is triggered.

At block 124, the slave application uses the available queryable files to run against the data store as instructed. The connection to the data store is managed through the local configuration previously cited in block 106. The novel queryable file format is compiled with injectable parameter instructions for fields like start and end dates to produce valid code that can be interpreted by the data store. These parameter values can be supplied by the master system from block 120 or from the local configuration as defined in block 106. According to one embodiment, the instructions for the slave application include the specific queryable file to use, injectable values to include (e.g., start date, end date, schema, and other), the target data store to compile to (e.g., Oracle, MS SQL, or other), and the target schema. The result of this compilation, in some embodiments, is valid SQL code with embedded values that achieve a data extraction with desired parameters for the targeted data store. Using the Code 1 example outlined above, the resultant code would compile to the following with these instructed parameters: a start date of Mar. 1, 2019, an end date of Mar. 2, 2019, and a schema of "test":

select id, name from test.sampleTable where start_date>='2019-03-01' and end_date<='2019-03-02'

Next in block 128, the slave application will compile a summary of the action against the data store. According to one embodiment, this will include characteristics of a query attempt like the number of rows found, the length of time required to evaluate the command, and pertinent error messages.

In block 130, the slave application transmits the query summary to the master system. This enables the master system to be in-sync with the slave system regarding the status of individual instructions and queries.

In block 132, the slave application securely transmits the results of the data store query. According to one embodiment, the result is exported in a standard data form like a comma separated values (CSV). Continuing the Code 1 example above, a CSV file is generated locally that would include columns for 'id' and 'name' values within the date range of Mar. 1, 2019 and Mar. 2, 2019 from the "test" schema. The file may be encrypted locally (e.g., envelope encryption) prior to export. Additionally, this file may then be compressed (e.g. gzip) to enable a smaller payload. It is then sent using a secure port and protocol to the endpoint (e.g. a network-accessible data storage service), which was previously defined and compiled within the slave application in block 102. The endpoint could also be located within the local configuration or overridden by the master system, according to some embodiments.

In block 134, the slave application will either proceed to the next instructed queryable file with its associated parameters or will go back to sleep. According to one embodiment, the slave application may reach out to the master system in order to allow further external control of this slave application loop. For example, a set of query instructions may be subsequently cancelled or have its parameters altered by the external administrator.

Figure 2:
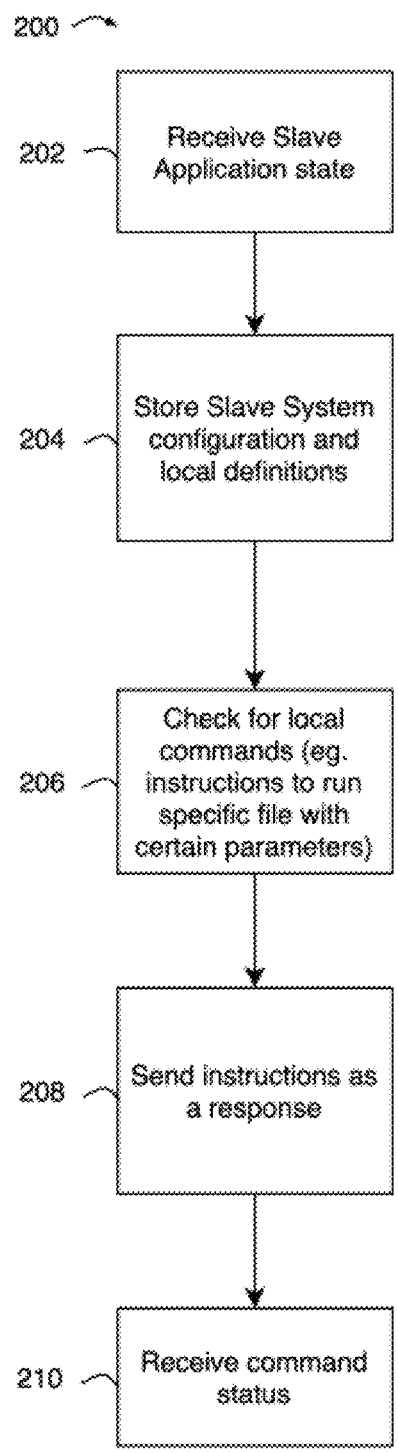
FIG. 2 is a flow diagram illustrating the method for a master system that exists outside of the inaccessible network. The master system responds to health checks from the slave system with instructions and parameters.

FIG. 2 is a flow diagram of an illustrative process 200 that may be implemented by the master system. It begins with block 202 where the master system receives a request with the local configuration from the slave application (which may have been sent at block 118 described above). Furthermore, this acts as a health check for the master system to recognize the slave application is live and functioning appropriately. A slave application that has not sent this health check within a defined period of time will trigger a notification (e.g., by email, SMS message, a notification within a dedicated application, and/or other method) to the external administrator or other configured stakeholder(s).

In block 204, the master system stores the configuration and state of the slave application. According to one embodiment, this information can be viewed in a user interface or otherwise for further insight and analysis by the external administrator. A sample administrator dashboard interface for analyzing performance of the slave application is furnished in FIGS. 4A, 4B, and 4C.

Self-healing capabilities are automatically applied to regularly scheduled processes of time series data. For example, there may be a process that runs daily to extract data from the previous day. If one of those files fails for the slave application, this error is communicated here to the master system which then generates and stores an indication of the missing file and day. The master system then will automatically furnish instructions locally for the next day's scheduled data to extract an additional day. In the Code 1 example above, a successful transaction for that day's data would result in the following compiled code the next day:

select id, name from test.sampleTable where start_date>='2019-03-02' and end_date<='2019-03-03'

However, an error for that day's data would automate instructions to expand to include the failed day and would result in the following compiled code the next day:

select id, name from test.sampleTable where start_date>='2019-03-01' and end_date<='2019-03-03'

In block 206, the master system will determine if instructions have been loaded. According to one embodiment, the instructions can be entered by a user via a graphical user interface. A sample administrator dashboard interface for inputting instructions for the slave application is furnished in FIG. 4D. The instructions may specify the query file and the injectable parameters like start and end dates. Beyond this manual entry, the master system also contains logic to automate predefined patterns of instruction that can be configured. For example, a "historical extraction" instruction will break a time series file down by monthly blocks for a given year, while a "daily extraction" automates the extraction of all time series data down to the previous day. As the slave application exists within an unreachable private network, these stored instructions enable a remote repository of the external administrator's commands without needing to directly access the slave application. The defined extraction instructions could be used to extract data that feeds into an analytics dashboard that provides insight into a complex data problem that exists for the data steward. An example of a web-based analytics dashboard that relies on this remote data is supplied in FIG. 5.

In block 208, the master system responds to the slave application request with the instructions and parameters specified as part of a manual request by the external administrator or a preconfigured automated process. Within the method of FIG. 1B described above, these instructions would then be received by the slave application at block 120. In block 210, the master system receives a response from the slave application after an attempt to execute the instructions against the data steward's data store. This response is stored in a local data repository for reference by other external applications.

Figure 3:
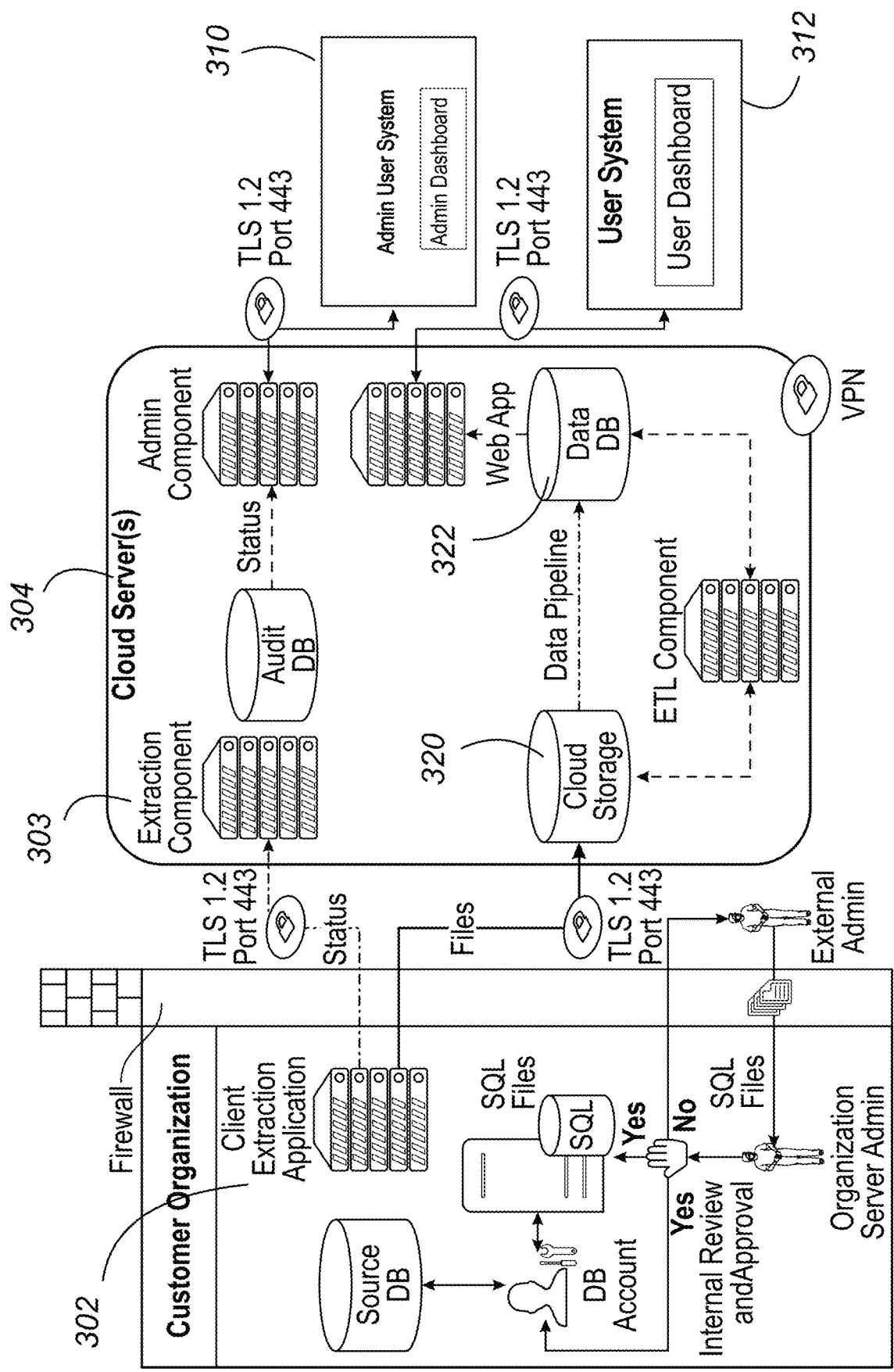
FIG. 3 illustrates an example operating environment for implementing aspects of the present disclosure, according to one embodiment.

FIG. 3 demonstrates an architecture and operating environment, according to one embodiment, involving the slave application (illustrated in this example as client extraction application 302) and the master system (implemented in the illustrated embodiment as extraction application 303 executed by the computing system 304) communicating through a firewall. The computing system 304 may be remote from the organization and firewall, and accessed over a network such as the Internet and/or via tunneled VPN or other method. According to one embodiment, the extracted data from block 132 is stored within a data store 320 (such as an AWS S3 repository). From here, it proceeds through a data pipeline where iterations of extract-transform-load (ETL) processes are employed. Ultimately, the data is transformed into a schema 322 (which may be stored in a data store) that serves a publicly facing application (which may include a user dashboard accessible via a user system 312) as demonstrated in FIG. 5. Additionally, the health checks sent from block 118 are stored within the master system (such as in the audit database in communication with extraction application 303) to furnish a separate private application for the external administrator (which may include an administrative dashboard accessible via an administrative user system 310) as is demonstrated in FIGS. 4A, 4B, 4C, and 4D.

FIG. 4A demonstrates a sample graphical interface associated with the master system that assists the external administrator with monitoring the system status across multiple data stewards. According to one embodiment, this summary view lists the data stewards with a slave application installed. As shown in an example card 402, some information listed can include the data steward's name, the time of the last health check received, the time of the last daily process executed, the scheduled time of the next automated daily process, the number of files available for the slave application, whether the previous extraction succeeded or failed, the names and contact information for the data steward, and whether an extraction is currently underway. Some of this information is received from the application and the rest is defined by the external administrator. Individual data steward detail can be further viewed by clicking on or otherwise selecting a panel or selectable option associated with a data steward.

FIG. 4B demonstrates a sample graphical interface that summarizes an individual data steward's details. According to one embodiment, this summary can be reached by the user clicking on or otherwise selecting a card like that seen in 402. This view lists each set of instructions (referred to as a process in the figure). One row, as exemplified by 404, may include a unique identifier, the date range for relevant time series data, and whether parts of it succeeded or failed. This information is intermittently received from the slave application and updated. Additional details about a specific set of instructions can be seen by clicking on it or otherwise selecting it within the interface.

FIG. 4C demonstrates a sample graphical interface that summarizes an individual set of instructions. According to one embodiment, this summary view can be reached by the user clicking or otherwise selecting a row like seen in 404. This summary lists each individual available queryable file run by the slave application, the time of execution, the number of files run, and the date ranges. When clicking on an individual queryable file, further details are displayed to include amount of data and number of rows extracted, the destination endpoint of any received logs from the slave application, the destination endpoint of the data extraction (e.g., path to compressed CSV file on AWS S3), and the compiled valid SQL command that was used.

FIG. 4D demonstrates a sample graphical interface that enables external administrators to load instructions for the slave application to pull upon subsequent health checks. This will typically be done within the context of a single data steward's installation. According to one embodiment, the external administrator can specify an extraction type that can automate instructions (e.g., "historical extraction", single "on demand extraction") like shown in 406, select a date range for time series data, and select files that are available on the slave application (this list is received from block 120). By submitting these instructions via item 408, the queryable files along with relevant parameters are loaded into the master system at block 206 and await the next slave application health check.

Figure 5:
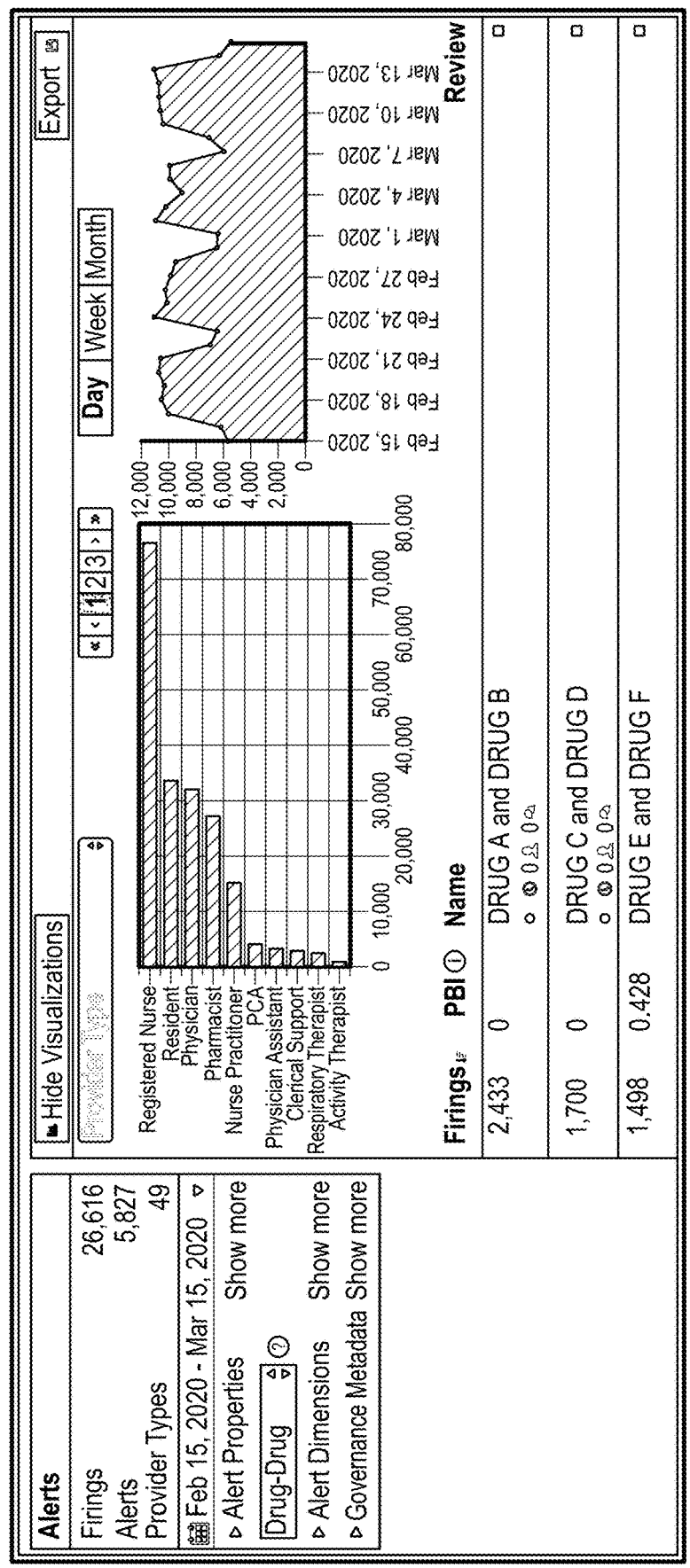
FIG. 5 illustrates an analytics dashboard that may be presented in a user interface viewed outside of a data steward's private network, but that relies in part on data extracted from the private network.

FIG. 5 demonstrates an example of a downstream analytics dashboard within the serviced application that lives outside of the data steward's private network, but relies on the extracted data. According to one embodiment, the ETL process can summarize counts of rows for a particular data extraction and then display them within data visualizations like bar or line charts. Tabular data can also be displayed that displays the names of data entities extracted as well as associated summary statistics derived from the extracted data. The serviced application may pull the status of available data as was previously mentioned in block 210 above. For example, a chart may show a "Data Loading" indicator or visualization if the ETL is in a pending or extracting state. On the other hand, a visualization like a bar chart or tabular data could be presented when the ETL flags that data has successfully extracted.

Figure 6:
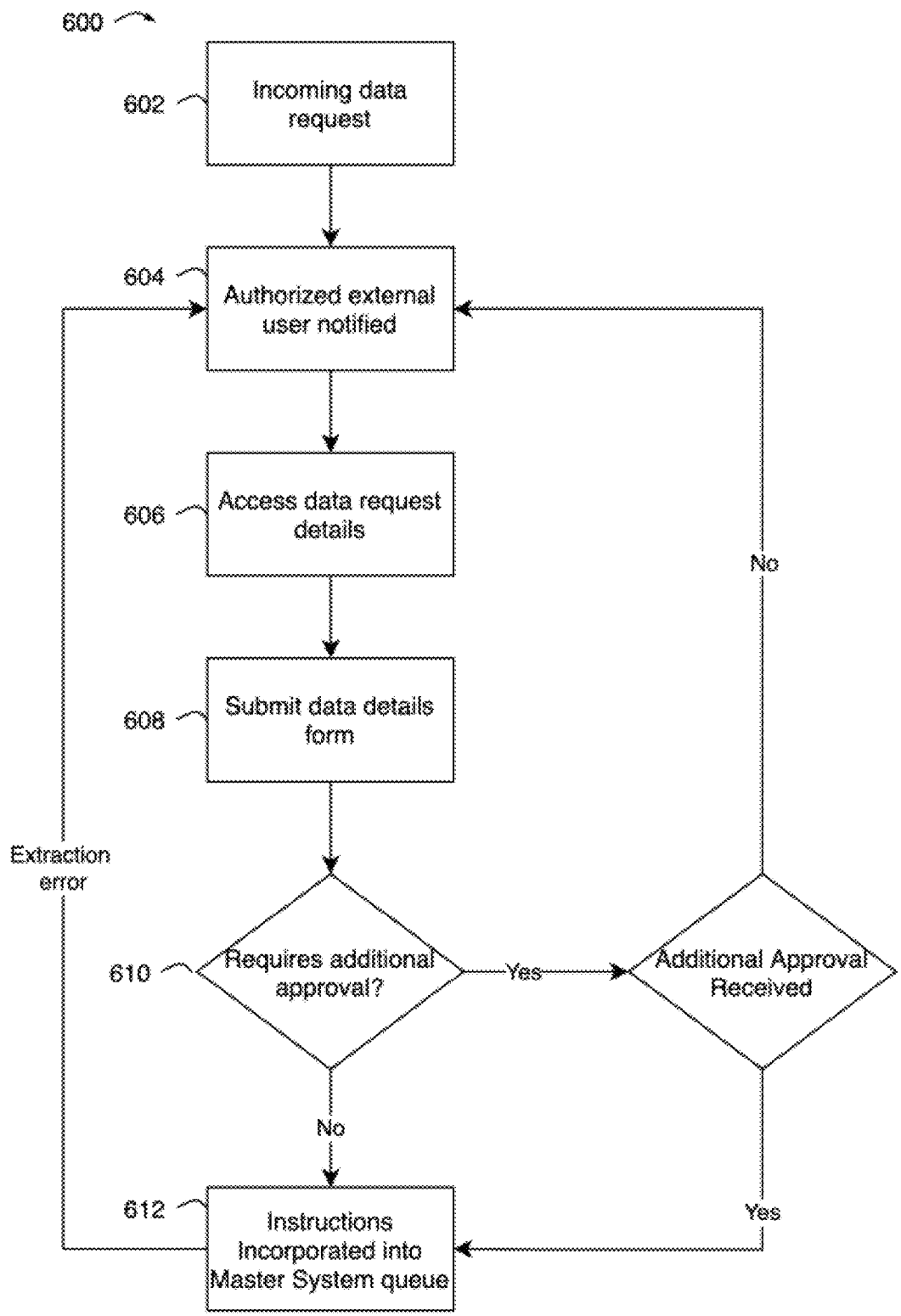
FIG. 6 is a flow diagram of an illustrative method for requesting, customizing, and authorizing cloud-based queryable assets, according to some embodiments.

FIG. 6 is a flow diagram of an illustrative method for requesting, customizing, and authorizing cloud-based queryable assets, according to some embodiments. The illustrative method 600 begins at block 602. According to one embodiment, the serviced application provides a graphical user interface for an end-user to make a data request. A data request may include a general description of the type of data requested, the use case for the data, the data store where the data may be available, and contact information of the requestor.

At block 604, the system notifies the authorized stakeholder after a new data request is submitted. An authorized stakeholder is typically a user approved by the data steward to make requests against their secured data stores. This notification (e.g., by email, SMS message, a notification within a dedicated application, and/or other method) provides details about the data request but may also include a web hyperlink or other referenceable endpoint that will include further details.

At block 606, the authorized stakeholder may view further details about the data request. The authorized stakeholder may navigate to the details about a data request via the notification referenced above in block 604. The data request may also be accessed via a list of all available data requests for a data steward. FIGS. 7A and 7B demonstrate dashboards intended for the authorized stakeholders in order to interact with data requests according to one embodiment. In these figures, a measure and cohort are similar to that of a variable that stores information about a data request. They represent different standardized structures for a data extract. Wherein a measure may include or reference a patient identifier and a value, a cohort may only include a patient identifier. For example, a measure name might be "Hospital Length of Stay" and the associated measure SQL definition would define target columns on the data steward's data store that extract data with both patient identifiers and how long the patient stayed in the hospital. Similarly, a cohort name might be "All Hospital Asthma Admissions" and the associated measure SQL definition would define target columns on the data steward's data store that extract data of unique identifiers for all patients admitted with a diagnosis of asthma.

Measures and cohorts can be joined together in the serviced application as previously demonstrated in FIG. 5 to show analytics, visualizations, and statistics. An example of a data request list, according to one embodiment, is shown in FIG. 7A. This dashboard example shows a list of the names of data requests, their requestors, their approval status, and extraction status. Depending on the authenticated user's security roles, the available data request list may be limited to an individual data steward's organization or multiple. In FIG. 7B, a dashboard for the authorized stakeholder detailing details of the data request is shown. According to one embodiment, details about the data request including, but not limited to, a description of the data needed, the requestor's contact information, the use case, and/or a potential target data store. These fields may be completely or partially populated from the form previously described in block 602.

At block 608, the authorized stakeholder enters data that will be fed into the master extractor system instructions queue as referenced in block 206. An illustrative data details submission form is again demonstrated in FIG. 7B. According to one embodiment, this form may include fields including, but not limited to, the data measure name, an easy-to-understand description that will be shown in the serviced application, a more technical definition not written in code, the data types, and a target data store and SQL query that will be included in the instructions stored in the master system. Rather than free-text fields, these submissions can also be performed via visual controls or interface elements within a graphical user interface. For example, a user may click through names of target tables and columns in the data steward's data store in order to subsequently generate a SQL query. Upon submission of the data request form at item 702, a subsequent view of this dashboard may show elements including, but not limited to, the individual components of the serviced application where the data is used, information about data owners/requestors, metrics and visualizations concerning performance of the extracts (e.g. number of rows extracted within a time period), and alternative versions of the data request as changes are made over time.

At block 610, the submitted data request may require further approval, in some embodiments and configurations. If configured by the data steward, additional authorized stakeholders would be notified, via similar methods as referenced in block 604, to approve the submission. At block 612, approved data request instructions are incorporated into the master system queue. As previously discussed in block 206, these instructions will be pulled down by the slave system upon the next status check. From block 210, if an error is encountered that pertains to the instruction itself (e.g. a requested table doesn't exist on the target data store), the authorized stakeholder will again be notified in order to remedy the problem.

Figure 8:
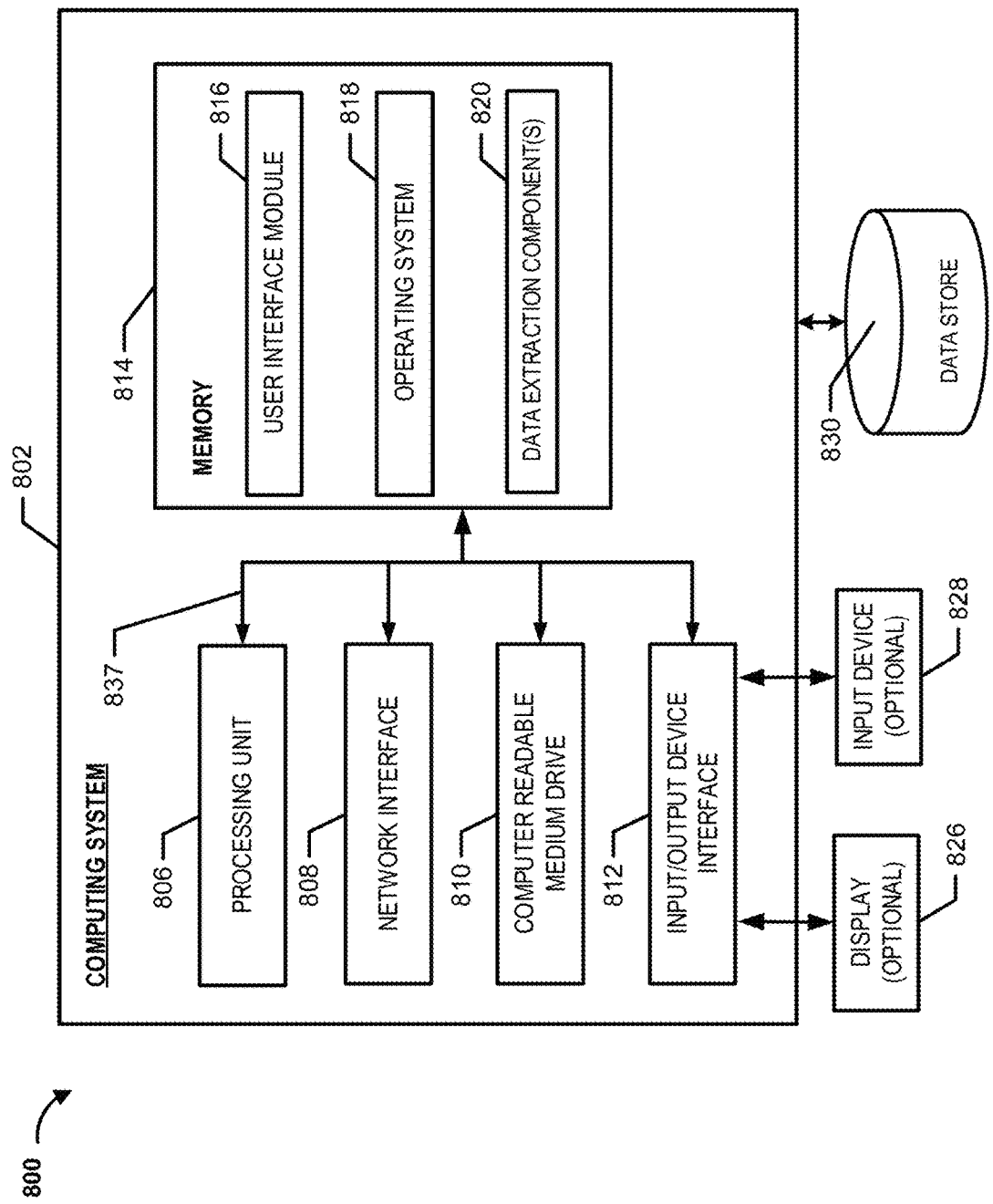
FIG. 8 illustrates a general architecture of a computing system that may be used to implement aspects of the present disclosure, according to some embodiments.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. It is not necessary, however, that all of these generally conventional elements be shown in order to provide an enabling disclosure. In some embodiments, the computing system 802 may be an example of what is referred to as the master system above or as computing system 304, though a customer organization's system that operates the slave application as described above may include one or more similar components (such as a display, processing unit, network interface, memory, operating system, etc.), in some embodiments.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more data extraction components 820, which may be executed by the processing unit 806 to perform operations according to various embodiments described herein. The components or modules 820 may access one or more data store 830 to store and/or retrieve data as described herein. The data store(s) may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks, such as the Internet. In particular, the computing system 802 may establish a communication link with a network (e.g., using known protocols) in order to send communications to another computing system over the network.

Those skilled in the art will recognize that the computing system 802 may be any of a number of computing systems including, but not limited to, a laptop, a personal computer, a mobile phone, a smartphone, a tablet computer, another wireless device, one or more servers, and the like.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
   memory; and
   a processor in communication with the memory and configured with processor-executable instructions to perform operations comprising:
   providing configuration information for a data extraction application operating behind a firewall on a client system;
   receiving application state information from the data extraction application, wherein the application state information is automatically gathered and sent by the data extraction application upon the data extraction application being awakened at a predetermined time;
   in response to receipt of the application state information, determining commands to return to the data extraction application that include one or more query parameters;
   sending the commands to the data extraction application, wherein the commands include the one or more query parameters as parameters to be injected by the data extraction application into at least one query previously stored by the data extraction application;

obtaining, from the client system or a data store outside of the firewall, results of the data extraction application executing the query with the parameters injected, wherein the query was executed by the data extraction application with respect to one or more files located behind the firewall;

identifying that data relating to a first time period was not extracted by the data extraction application as specified by one of (a) a predetermined schedule or (b) a request from the computer system; and sending a set of commands to the data extraction application related to a second time period that causes the data extraction application to extract both (c) data related to the first time period and (d) data related to the second time period.

2. The computer system of claim 1, wherein the client system comprises or is in communication with one of (a) an electronic health record system or (b) a computer system of a medical practice, wherein the one or more files located behind the firewall are stored in association with at least one of the electronic health record system or the medical practice.

3. The computer system of claim 2, wherein the at least one query previously stored by the data extraction application is configured, when executed with the one or more query parameters, to access electronic health data behind the firewall.

4. The computer system of claim 1, wherein the operations further comprise monitoring, by the computer system, a plurality of systems or subsystems of the client system based on the obtained results of the data extraction application, wherein the computer system is not permitted to directly access data of the plurality of systems or subsystems of the client system.

5. The computer system of claim 1, wherein the operations further comprise:

generating a user interface that includes a plurality of metrics derived from the obtained results of the data extraction application that operates behind the firewall on the client system; and causing presentation of the user interface to an administrator computing device that is not configured to directly access files behind the firewall on the client system.

6. The computer system of claim 5, wherein the user interface further includes at least one metric or portion of information derived from data retrieved by the computer system from a second computer system that is not located behind the firewall.

7. A computer-implemented method comprising, as implemented by one or more processors configured with specific executable instructions:

providing configuration information for a data extraction application operating behind a firewall on a client system;

receiving application state information from the data extraction application, wherein the application state information is automatically gathered and sent by the data extraction application upon the data extraction application being awakened at a predetermined time;

in response to receipt of the application state information, determining commands to return to the data extraction application that include one or more query parameters;

sending the commands to the data extraction application, wherein the commands include the one or more query parameters as parameters to be injected by the data extraction application into at least one query previously stored by the data extraction application;

obtaining, from the client system or a data store outside of the firewall, results of the data extraction application executing the query with the parameters injected, wherein the query was executed by the data extraction application with respect to one or more files located behind the firewall;

identifying that data relating to a first time period was not extracted by the data extraction application as specified by one of (a) a predetermined schedule or (b) a request remotely sent to the data extraction application; and sending a set of commands to the data extraction application related to a second time period that causes the data extraction application to extract both (c) data related to the first time period and (d) data related to the second time period.

8. The computer-implemented method of claim 7, wherein the client system comprises or is in communication with one of (a) an electronic health record system or (b) a computer system of a medical practice, wherein the one or more files located behind the firewall are stored in association with at least one of the electronic health record system or the medical practice.

9. The computer-implemented method of claim 7, wherein the at least one query previously stored by the data extraction application is configured, when executed with the one or more query parameters, to access electronic health data behind the firewall.

10. The computer-implemented method of claim 7, further comprising monitoring, by the computer system, a plurality of systems or subsystems of the client system based on the obtained results of the data extraction application, wherein a computer system implementing the computer-implemented method is not permitted to directly access data of the plurality of systems or subsystems of the client system.

11. The computer-implemented method of claim 7, further comprising:

generating a user interface that includes a plurality of metrics derived from the obtained results of the data extraction application that operates behind the firewall on the client system; and causing presentation of the user interface to an administrator computing device that is not configured to directly access files behind the firewall on the client system.

12. The computer-implemented method of claim 11, wherein the user interface further includes at least one metric or portion of information derived from data retrieved from a second computer system that is not located behind the firewall.

* * * * *